(12) United States Patent
Salkowski (10) Patent No.: US 9,639,661 B2
(45) Date of Patent: May 2, 2017

(54) SIMULATOR FOR BREAST IMAGING EXAMINATIONS

(71) Applicant: Wisconsin Alumni Research Foundation, Madison, WI (US)

(72) Inventor: Lonie Salkowski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 271 days.

(21) Appl. No.: 14/027,772

(22) Filed: Sep. 16, 2013

(65) Prior Publication Data

US 2015/0079566 A1 Mar. 19, 2015

(51) Int. Cl.
| | | |
|---|---|---|
| G06K 9/00 | (2006.01) | |
| G06F 19/00 | (2011.01) | |
| G09B 23/28 | (2006.01) | |
| G06T 7/00 | (2017.01) | |

(52) U.S. Cl.
CPC .......... *G06F 19/321* (2013.01); *G06T 7/0014* (2013.01); *G09B 23/286* (2013.01); *G06T 2207/10116* (2013.01); *G06T 2207/30068* (2013.01)

(58) Field of Classification Search
CPC ......... G06T 2207/30068; G06T 7/0012; G06T 2207/20076; G06T 2210/41; G06K 2209/05; G06K 9/6277
See application file for complete search history.

(56) References Cited

U.S. PATENT DOCUMENTS

| | | | | |
|---|---|---|---|---|
| 6,669,482 | B1 * | 12/2003 | Shile | 434/262 |
| 2002/0131625 | A1 * | 9/2002 | Vining et al. | 382/128 |
| 2007/0232868 | A1 * | 10/2007 | Reiner | 600/300 |
| 2007/0280525 | A1 * | 12/2007 | Basilico et al. | 382/132 |
| 2010/0169116 | A1 * | 7/2010 | Marx | 705/2 |
| 2011/0052025 | A1 * | 3/2011 | Highnam et al. | 382/131 |
| 2011/0137132 | A1 * | 6/2011 | Gustafson | 600/300 |
| 2012/0185292 | A1 * | 7/2012 | Hahn et al. | 705/7.21 |
| 2012/0294502 | A1 * | 11/2012 | Chan et al. | 382/131 |
| 2015/0046875 | A1 * | 2/2015 | Xu et al. | 715/834 |

OTHER PUBLICATIONS

Carney at al., May 2013, Diagnostic Mammography: Identifying Minimally Acceptable Interpretive Performance Criteria, radiology. rsna.org, vol. 267: No. 2, pp. 359-367.*

* cited by examiner

*Primary Examiner* — Vu Le
*Assistant Examiner* — Guillermo Rivera-Martinez
(74) *Attorney, Agent, or Firm* — Boyle Fredrickson, S.C.

(57) ABSTRACT

A system simulating the reviewing process of breast imaging examination (i.e. mammographic) information provides a data file of breast imaging information including mammographic (and other breast imaging examinations) images that may be scored by a trainee on computerized worksheet and expert assessments of those images. Quantitative data in the expert assessment may be compared to trainee-entered data recovered from the worksheet to provide an assessment of trainee proficiency in interpreting breast imaging studies. The data file of breast imaging information may be derived from actual clinical data anonymized and selected to provide for realistic yet demanding simulation.

20 Claims, 5 Drawing Sheets

| 50 | MAMMOGRAPHY EXAMINATION | CHRISTINE JADE ANDERSON, PENRAD MAIN CLINIC | 3/17/2011 10:34:34 |
| STACY E. PENRAD DOB: 06/06/1949 AGE:61 F PID: 123654789 |

TISSUE DENSITY − SCATTERED FIBRO. +
ADD ABNORMALITY RIGHT
DETAIL RIGHT | CLEAR
SIZE: −0.5 cm
LOCATION: 45°
— 76

RIGHT SPECIALS
ADD TARGETED ULTRASOUND
+NONE   −RIGHT
−BILATERAL  −LEFT

PROCEDURES | COMPARE
PRE EXAM | CLONE PREV

FILMS USED  MEDIOLATERAL / OBLIQUE VIEW
RIGHT  72  SUPERIOR  72  LEFT
74
INFERIOR
RIGHT   LATERAL   LEFT
CAD BENEFIT
<N/A> 74
NEUTRAL
−MINUS
+PLUS
MEDIAL  72
CRANIOCAUDAL VIEW
SCREENING, BILATERAL, DIGITAL, WITH CAD

ADD TEXT | ADVANCED SPECIALS | APPROVE / PREVIEW | EXIT | HELP

TISSUE DENSITY − SCATTERED FIBRO. +
ADD ABNORMALITY LEFT
DETAIL LEFT | CLEAR
SIZE: 1.6 cm
LOCATION: 45°
6 O'CLOCK
INFERIOR MEDIAL MIDDLE
— 76

LEFT SPECIALS
MAMMOGRAM BI-RADS
3: PROBABLY BENIGN ▼
MANUAL OVERRIDE
56    70
52

77 — FINAL RESULTS / RECOMMENDATION (BASED ON SCREENING INFORMATION)
1. WHAT IS THE LIKELIHOOD THAT THIS FINDING WILL LEAD TO A BIOPSY?

| 0 | 1-10% | 11-25% | 26-50% | 51-75% | 76-99% | 100% |
|---|---|---|---|---|---|---|
|   |   |   |   |   |   |   |

83    85

2. IF THIS FINDING REQUIRES A BIOPSY, WITH THE INFORMATION YOU HAVE SO FAR, HOW WOULD YOU PROCEED TO BIOPSY?

| NO BIOPSY | |
| NEEDLE LOCALIZATION AND SURGICAL EXCISION | |
| STEROTACTIC BIOPSY | |
| ULTRASOUND GUIDED BIOPSY | |

89    87

COMMENTS:
3. FOR THOSE FINDINGS THAT REQUIRE BIOPSY, WHAT IS YOUR PREDICTED PROBABILITY THAT THIS FINDING WILL A CANCER?
(CHECK ONE BOX)

| PPV | 0 | <2% | 3-14% | 15-47% | 48-94% | >95% |
|---|---|---|---|---|---|---|
| BIRADS | B2 | B3 | B4a | B4b | B4c | B5 |
| YOUR PREDICTION | | | | | | |

| BIRADS | CATEGORY ERRORS | PREDICTION ACCURACY | MASS IDENTIFICATION |
|--------|-----------------|---------------------|---------------------|
| 1,2 | 0 | — | — |
| 0 | 2 | 90% | +1 |
|   |   |     | −0 |

FIG. 6

SIMULATOR FOR BREAST IMAGING EXAMINATIONS

BACKGROUND OF THE INVENTION

The present invention relates to breast imaging and in particular to a computerized simulator for training and testing of individuals performing analysis of screening and diagnostic breast images.

Breast cancer is the second leading cause of death in women and the most common cancer in women in the United States. Screening mammography is the only current exam that increases the detection of early clinically occult breast cancers in women of average risk.

Mammography uses low energy x-rays to provide a radiographic image of breast tissue typically under mild compression. The radiographic image can reveal masses, asymmetries, architectural distortion or microcalcifications associated with breast cancer when reviewed by a trained professional.

The results of mammographic imaging are typically provided in the form of a prose clinical report describing features of the mammogram and clinical impressions. Included with the report will often be a ranking expressed in terms of a BI-RADS (Breast Imaging-Reporting and Data System) assessment category ranging from 0-6. In the BI-RADS ranking, categories 1 and 2 are normal or benign, category 3 is probably benign, categories 4 and 5 indicate a suspicion or likelihood of malignancy, and category 6 reflects imaging of a patient with a known diagnosis of breast cancer prior to definitive treatment. Normally a category 0 assessment during a screening mammogram will result in a recall for additional imaging.

The interpretation of mammograms is a complex process requiring a significant level of experience-honed judgment. For this reason, training in the interpretation of mammograms is normally done by parallel assessments of current cases by an experienced clinician working together in a one-on-one session with the individual to be trained. Although such training is extremely valuable in obtaining competency, the need for and format of one-on-one training sessions of this type understandably limits the opportunity for such training.

SUMMARY OF THE INVENTION

The present inventor has recognized that valuable ancillary training can be obtained on an automated basis by using a set of mammographic images that have been pre-characterized by an expert. For this purpose, much of the complexity of a clinical evaluation can be usefully simplified to a trainee's assessment of the BI-RADS or similar categories reflecting whether a recall for additional imaging would be required. A similar simplification may be used to obtain a more nuanced assessment of the trainee's understanding by soliciting a prediction of the likely BI-RADS results of that follow-up imaging. Unlike in an actual screening where an expert does not know the outcome of subsequent screening or a biopsy, the expert's characterization of the mammographic images in the simulation may optionally be informed by after-the-fact knowledge about the case (e.g. subsequent screening and/or biopsy) to provide an extremely high level of effective expertise.

Specifically, the present invention provides a simulator for breast imaging (mammograms, ultrasound, etc.) including a medical grade computer display and a data input device communicating with an electronic computer. The computer memory may hold a data structure having multiple records linking breast imaging studies to expert recall instructions, the latter indicating whether a patient associated with each mammographic image should be recalled for additional imaging based on the mammographic image. During operation, the computer executes a stored program to successively read the records of the data structure and, for each record, to display at least one mammographic image of the record and receive input through the trainee input device indicating a trainee recommended recall instruction. After reviewing of the records is complete, the program outputs a report indicating divergence between the trainee recommended recall instructions and the expert recall instructions.

It is thus a feature of at least one embodiment of the invention to provide an automatable method of training and assessing the interpretation of mammographic images. By identifying quantitative, computer-readable features of the diagnosis (for example BI-RADS categories) meaningful automated evaluation can be performed while maintaining a realistic clinical setting.

The records of the data structure may provide expert recall instructions that are predominantly instructions for no recall.

It is thus a feature of at least one embodiment of the invention to provide a simulation experience that is roughly analogous to real world practice in which most screenings do not result in a recall.

Nevertheless, the records of the data structure may provide expert recall instructions instructing recall of the patient greater than a normal expected percentage of five to twelve percent. For example, the expert recall instructions may instruct recall of the patient for greater than 20 percent and as high as 25 percent of the records, to enhance the learning experience and provide appropriate feedback where user has difficulty.

It is thus a feature of at least one embodiment of the invention to provide a more engaging and better training experience by increasing the recall rate above that found in a typical population.

The after-recall assessments may be encoded as numeric BI-RAD scores.

It is thus a feature of at least one embodiment of the invention to make use of a familiar and well-established scoring technique for automatic skill comparison and assessment.

The simulator may further receive input through the data input device indicating a trainee predicted "after-recall" assessment predicting an assessment after the patient of the record is recalled for further imaging and analysis and the records of the data structure may further provide an expert "after-recall" assessment indicating the ultimate assessment of the patient. In this case, the output report may indicate a divergence between trainee predicted "after-recall" assessment and expert "after-recall" assessment. This prediction may further include a numeric likelihood of biopsy and a type of biopsy.

It is thus a feature of at least one embodiment of the invention to derive greater insight into the understanding of the trainee beyond the readily quantified recall recommendation, by having the trainee classify the findings, predict the likely results of that recall and optionally whether a biopsy will be required and the type of biopsy. As before, this prediction may be captured by machine-readable numeric scores.

The simulator may further receive input through the data input device indicating a trainee-determined location and description of the suspicious imaging finding on the mammographic image of each record and the records of the data structure may provide expert-determined location of suspicious imaging findings (masses, calcifications, etc) on the mammographic image of each record. In this case, the output report may indicate a divergence between trainee-determined locations of suspicious imaging finding and expert-determined locations of suspicious imaging findings informed by positional error between the trainee-determined location of suspicious imaging finding and the expert-determined location of suspicious imaging findings.

It is thus a feature of at least one embodiment of the invention to provide an automatic analysis of a trainee's identification of one or more suspicious imaging findings.

The monitor may provide a patient clinical history associated with each record.

It is thus a feature of at least one embodiment of the invention to allow the trainee to take into account extrinsic information about the patient such as may assist in the analysis of the breast imaging study.

The records of the data structure may provide records reflecting a normal age distribution. Alternatively or in addition, the records may reflect a normal distribution of breast tissue density types.

It is thus a feature of at least one embodiment of the invention to provide a simulation that to the extent practical reflects a typical population of patients.

The data structure may include no less than 50 records.

It is thus a feature of at least one embodiment of the invention to provide reports that have statistical significance and that provide suitable training opportunity.

The simulator may provide a time limit for performing a given number of reviews and may permit a given review to be postponed while ultimately requiring completion of any postponed reviews by including them in the report regardless of whether they are subsequently completed.

It is thus a feature of at least one embodiment of the invention to provide a natural working environment where reviews may be made out of order while preventing subversion of the evaluative aspects of the simulation that might occur if different individuals reviewed self-selected different cases.

These particular objects and advantages may apply to only some embodiments falling within the claims and thus do not define the scope of the invention.

DETAILED DESCRIPTION OF THE PREFERRED EMBODIMENT

Figure 1:
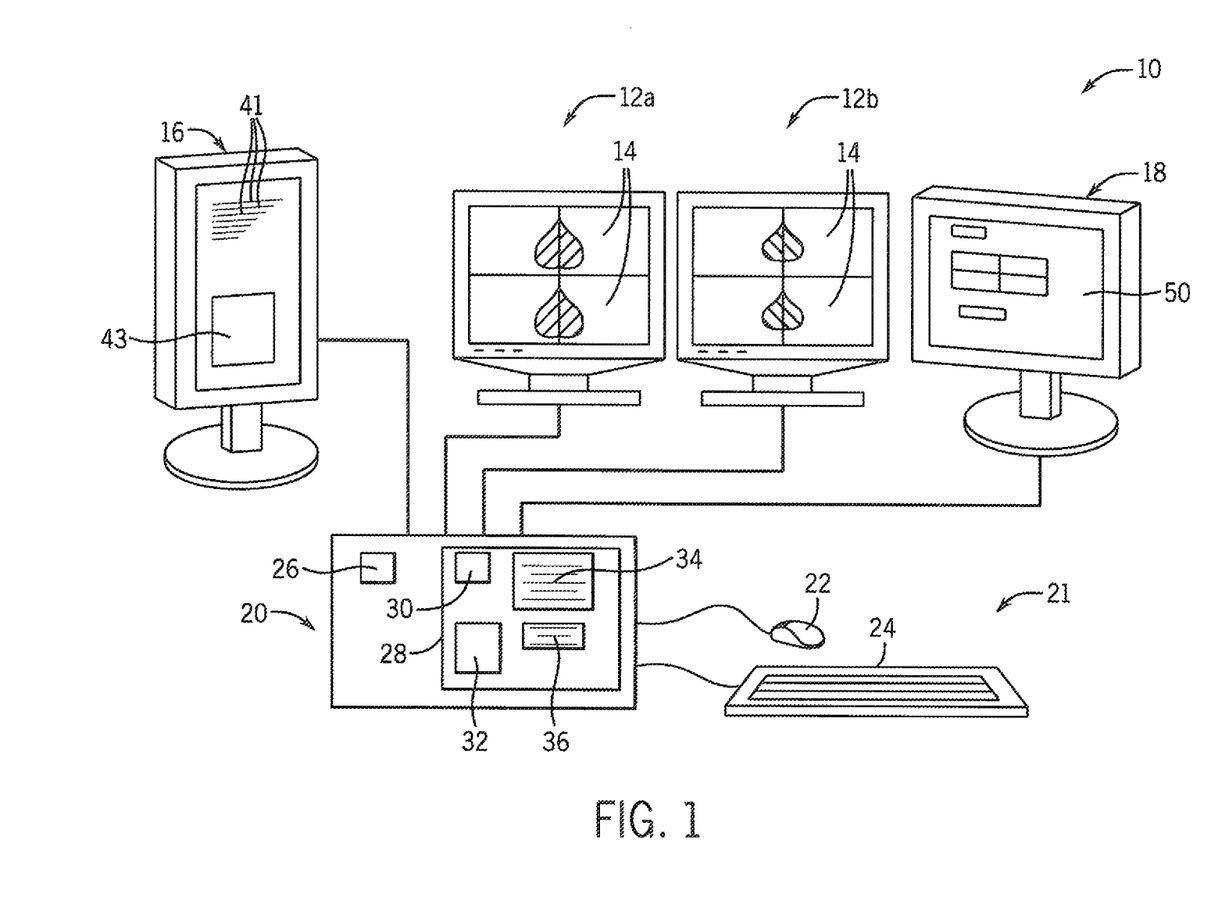
FIG. 1 is a block diagram of a simulation system according to the present invention providing a display of a data file of breast imaging (mammograms, for example) information by a computer for evaluation by a trainee and an input monitor for a worksheet to be completed by the trainee for evaluating that breast imaging information.

Referring now to FIG. 1, a simulator 10 for mammographic image viewing may provide mammography display monitors 12a and 12b for displaying mammographic images 14 of the type acquired with an x-ray mammography unit (not shown). The display monitors 12 will generally provide for at least five megapixel nominal resolution (for example, ten bit pixel resolution and 2048 by 2056 pixels) and will meet the standards of DICOM GSMF Part 14.

A work list monitor 16 may also be provided to display a list of cases in which mammograms or other breast imaging studies need to be reviewed and a report input monitor 18 into which clinical report data may be entered by a trainee. The work list monitor 16 and report input monitor 18 may be standard computer monitors.

Each of the monitors 12, 16, and 18 may connect to a simulation computer 20 also connecting to data input devices 21 including, for example, a mouse 22 and keyboard 24 according to techniques and standards well understood in the art. The simulation computer 20 may be a standard desktop computer, for example, capable of running the Windows operating system. The simulation computer 20 may include one or more processors 26 communicating with an electronic memory 28. The electronic memory 28 may be a logical combination of multiple memory devices including random access memory, disk drive memory and the like.

The electronic memory 28 may hold a commercially available operating system 30 as well as a simulation program 32 of the present invention as will be described below. In addition, the electronic memory 28 may hold a simulation data file 34 providing data for simulated patient cases that will be reviewed by the trainee and a trainee data file 36 holding information entered by the trainee during the simulation process.

Figure 2:
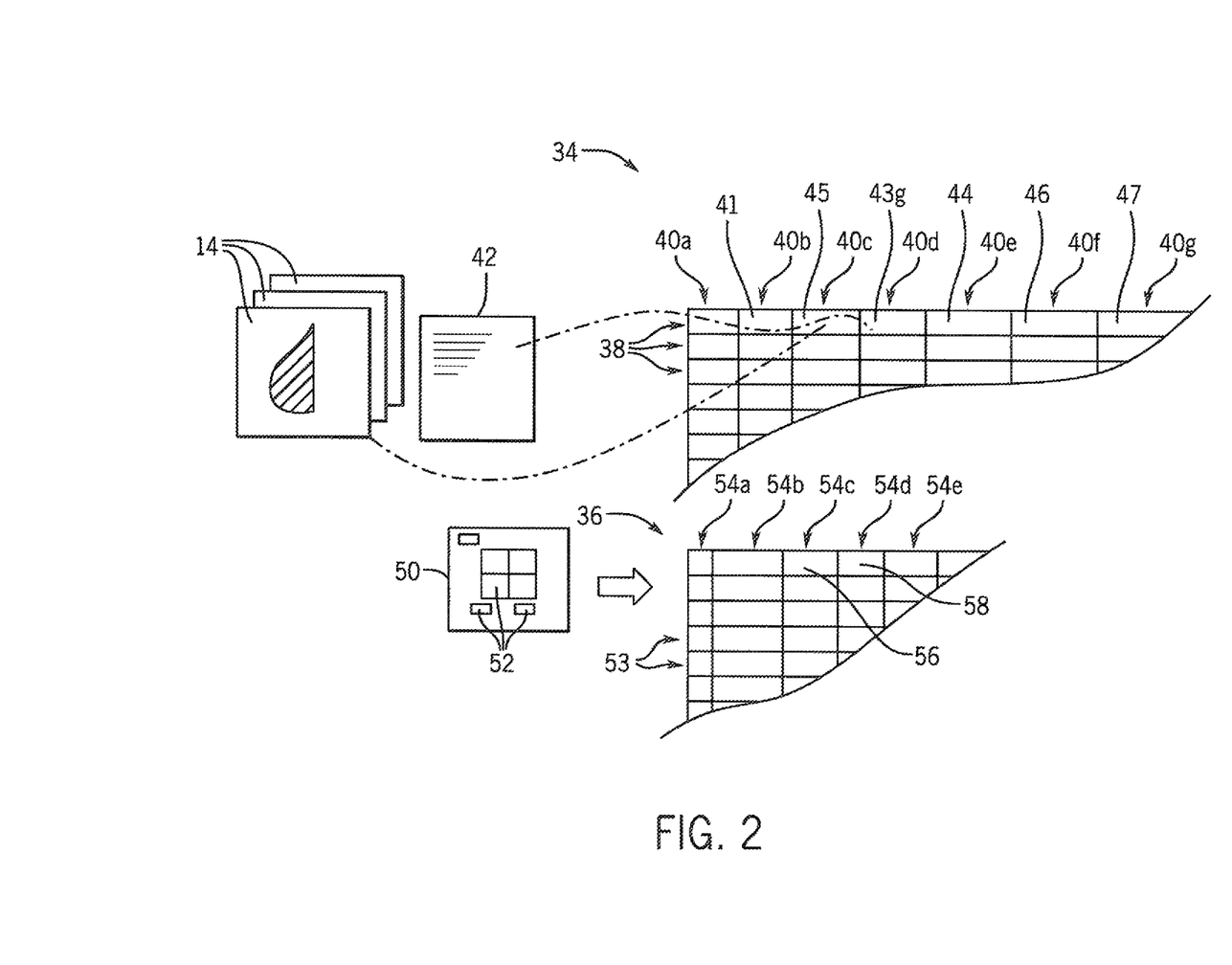
FIG. 2 is a logical diagram of the data file of breast imaging information of FIG. 1 and a similar data file for receiving input from the trainee evaluating the breast imaging information.

Referring now to FIG. 2, the simulation data file 34 may be represented as a logical table having records 38 (represented by rows), each corresponding to a different patient, holding data associated with a breast imaging exam in various attributes 40 (represented by columns). A first attribute 40a may provide a record number, for example, an integer from one to the total number of records in the simulation data file 34. In a preferred embodiment, the simulation data file 34 will include at least 100 records and typically more than 50 records. This record number will be used to match records 38 in the simulation data file 34 with corresponding records in the trainee data file 36.

A second attribute 40b may provide for a patient identifier that has been anonymized so as not to identify an actual patient. This patient identifier may be a number or a pseudonym.

A third attribute 40c provides a breast imaging exam file 45 including one or more digitized mammographic images (or comparable other breast imaging study; for example ultrasound, MR, tomography) 14 associated with the patient of records 38. Generally the mammographic images 14 will include left and right mediolateral oblique images and left and right craniocaudal images meeting DICOM standards. In one embodiment, the mammographic images 14 may include some text providing imaging parameters such as: laterality, image view, and radiation dose parameters (kVp, milliamps, compression thickness target and filter) but are otherwise free of any identification of an actual patient or any data indicating diagnostic conclusions.

A fourth attribute 40*d* may provide for an abbreviated patient history 42 in text form, for example, noting previous breast imaging studies in their dates, family history of breast cancer, patient identified concerns, history of pregnancies if any and the like for the patient of the records 38.

A fifth attribute 40*e* provides an expert recall instruction 44 prepared by an expert having reviewed the data of attributes 40*c* and 40*d* and optionally having after-the-fact knowledge of the results of any later history on the patient including a recall examination, biopsy, and the like. The expert recall instruction 44 thus provides, to the greatest practical extent, a correct diagnosis based on the breast imaging exam information informed not only by experience but also by history on the patient. Generally the expert recall instruction 44 will be in the form of a BI-RADS rating of 0, 1, or 2 being the range typically provided after reviewing a screening mammogram according the following table:

TABLE I

| BI-RADS Assessment Category | Category Title |
|---|---|
| 0 | Need additional evaluation |
| 1 | Normal |
| 2 | Benign |
| 3 | Probably benign |
| 4 | Suspicion of malignancy |
| 5 | Highly suggestive of malignancy |
| 6 | Known biopsy-proven malignancy |

Note that while the expert recall instruction 44 is informed by the ultimate history of the patient, for example the results of a follow-up biopsy, the recommendation is made from the point of view of an expert viewing the mammographic images 14 and reviewing the patient history 42 only, and thus may indicate a BI-RADS category of 4 or 5, for example, in cases both where history proves a known malignancy or absence of a malignancy. That is, the expert recall instruction 44 represents a nearly infallible expert without knowledge of the future.

In addition, an attribute 40*f* is provided for those records 38 having an expert recall instruction 44 of BI-RADS 4 or 5. This attribute 40*f* provides one or more expert predictions 46 including a likelihood that a recall for a second imaging session will lead to a requirement of biopsy (after-recall), a conditional prediction of a type of biopsy that will be required if biopsy is indicated, and a conditional prediction if a biopsy is required as to whether cancer will be detected (an expert predicted "after-recall" assessment). Again these predictions are informed by the patient history and the information in the simulation data file 34 but represent the viewpoint of the nearly infallible expert without knowledge of the future.

Finally, attributes 40*g* may store the coordinates 47 of any suspicious breast imaging finding identifiable from the breast imaging images 14 as informed by subsequent patient history but from the viewpoint of an expert without knowledge of the future.

The records 38 each may represent actual patients whose data has been anonymized. Desirably the set of records 38 is selected from a larger set of actual patient records to provide a distribution of different ages that represents a realistic population. For example, the age distribution of the records 38 may desirably conform approximately to the following table:

TABLE II

| <39 years | 40-49 years | 50-59 years | 60-69 years | >70 years |
|---|---|---|---|---|
| 2% | 23% | 33% | 28% | 14% |

In addition, the records 38 may be selected among actual records of patients to provide a distribution of breast tissue types (breast fiboglandular tissue density), for example, corresponding proximately to the following table:

TABLE III

| fatty (<25% glandular) | Scattered (25-50% glandular) | Heterogeneous (51-75% glandular) | Extremely dense (<75% glandular) |
|---|---|---|---|
| 8% | 49% | 39% | 4% |

The number of recall instructions typical in mammographic screening of a general population will vary from 5 to 12 percent; however, the simulation data file 34 is adjusted to provide for more recalls in order to maintain the interest level of the trainee and to provide for a more intense training experience. In one embodiment, the records 38 of simulation data file 34 will provide for 75% expert recall instructions 44 of BI-RAD categories 1 or 2 (no recall) and 25% expert recall instructions 44 of BI-RADS category 0 (recall).

The records 38 are selected so that within the 25% associated with expert recall instructions 44 of BI-RADS 0.17% will ultimately be classified as BI-RADS 1 or 2; 7% will ultimately be classified as BI-RADS 4 and 1% will ultimately be classified as BI-RADS 5. These percentages are based on the total number of records 38.

Of the 25% of records 38 having expert recall instructions 44 of BI-RADS 0 that would, upon recall, then be classified as classified BI-RADS 4, 4% will have an expert BI-RADS subcategory of 4a (low suspicion of malignancy), 2% will have an expert BI-RADS subcategory of 4b (intermediate suspicion of malignancy), and 1% will have an expert BI-RADS subcategory of 4c (the moderate concern, but not classic for malignancy).

Referring now to FIGS. 1 and 2, the trainee in reviewing the information from each record 38 on the monitors 12, 16 and 18, may enter his or her assessment on a worksheet 50 displayed on the report input monitor 18. Generally, the worksheet 50 will provide for a number of data entry points 52 such as text record boxes, pulldown menus, and the like that may receive data entered by the trainee to be recorded in a trainee data file 36 in machine-readable form. In one embodiment, the worksheet 50 may include data entry points 52 mimicking those in commercial worksheets, such as the PenRad MIS system commercially available from PenRad™ Technologies Inc. of Buffalo, Minn., USA. A representation of portions of the PenRad MIS worksheet will be used in part in the following description of the invention; however, it should be appreciated that the invention is not limited to a particular commercial system or format.

Referring in particular to FIG. 2, data from the data entry points 52 on the worksheet 50 may be stored in records 53 of trainee data file 36, the former records 53 corresponding individually and in number to each of the records 38 in the simulation data file 34. In this respect, for example, each record 53 may include attribute 54a providing a record number matching one of the record numbers of attribute 40a of the simulation data file 34.

Generally, it will be of interest to capture all data entered by the trainee at data entry points 52 in the worksheet 50 even if they are not used in the assessment provided by the present invention. Attribute 54b will hold this data including, for example, text descriptions of the trainee's assessment of the mammogram. All data collected could be used to provide insight into the trainee's evaluation process for breast imaging studies and thus reveal areas needing remediation.

Data specifically associated with a trainee recall instruction 56 (corresponding to the expert recall instruction 44 although not necessarily in value) will be captured in attribute 54e described above. This trainee recall instruction 56 provides the trainee's best diagnosis based on the collaboration of information from the mammographic images 14 and patient history 42 expressed in the form of a BI-RADS assessment number (e.g. 0 1, one, or 2).

Attribute 54d may store multiple trainee predictions 58 (corresponding generally to the expert predictions 46 although not necessarily in value) described above.

Finally, the data file 36 may also include attribute 54e capturing locations for one or more suspicious imaging findings that may be identified by the trainee to be compared against the data of attribute 40g for the corresponding record 38.

Figure 3:
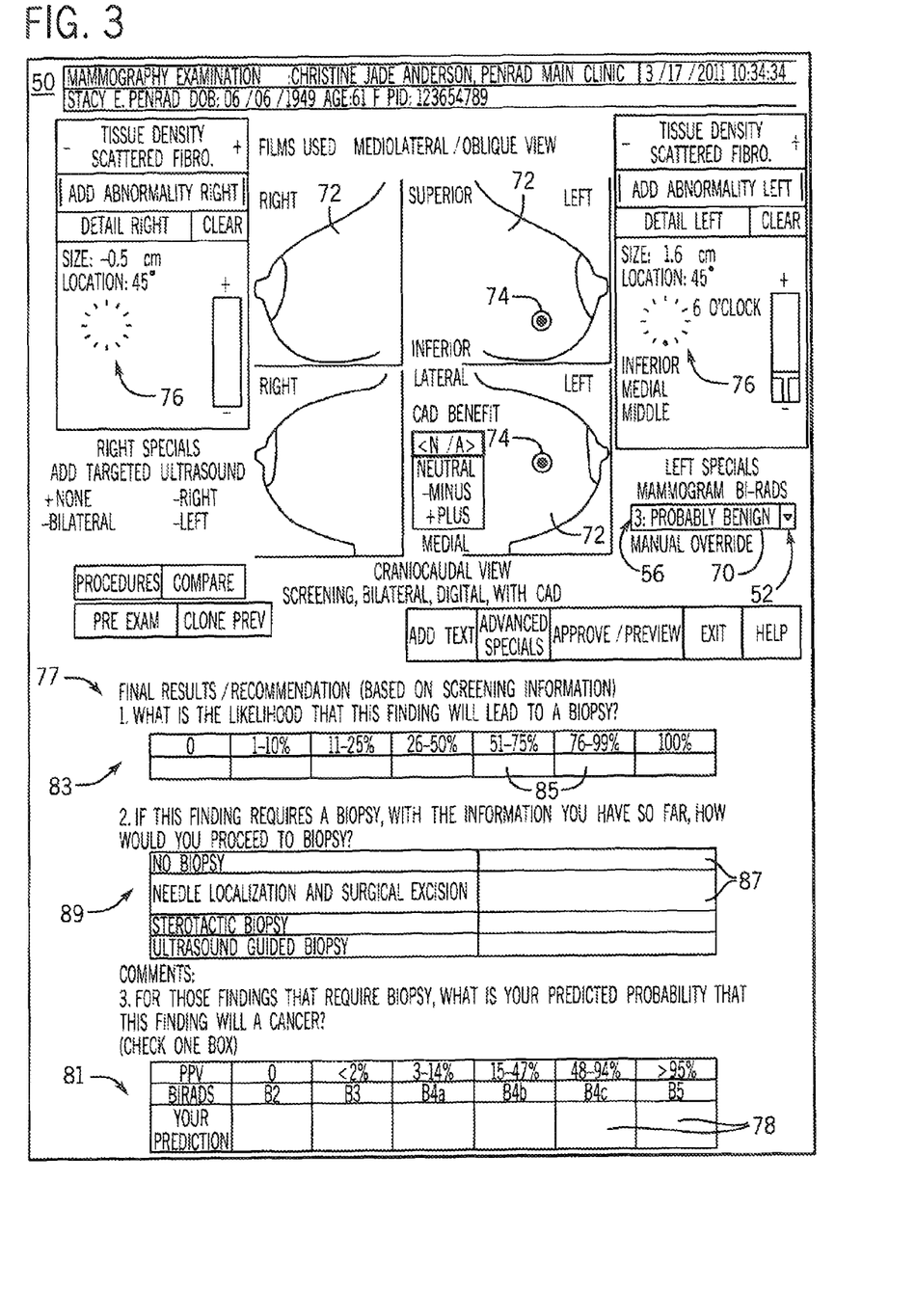
FIG. 3 is an example worksheet presented on the input monitor for use by the trainee in entering data related to evaluations of the breast imaging (i.e. mammographic) information.

Referring now to FIG. 3, more specifically, the worksheet 50 may provide a text box 70 into which the BI-RAD category of the trainee recall instruction 56 selected by the trainee may be entered after reviewing the mammographic information of a given record 53. This data may be typed into the text box 70 or entered by means of a pulldown menu or the like.

The worksheet 50 may present simplified depictions 72 of mammographic images 14 on which the trainee may locate the positions of any suspicious imaging finding evident in the mammographic images 14 by means of position markers 74. The position markers 74 may be located on both mediolateral oblique images and cranio caudal images to provide three dimensions of a Cartesian coordinate for the suspicious imaging finding (mass, calcifications, etc). The positional accuracy of this coordinate may be augmented by clock faces 76 showing approximate angular location of the imaging finding in the anterior-posterior direction. As noted above, the coordinates of one or inure located imaging findings may be stored in attribute 54e.

In one embodiment of the invention, the worksheet 50 may include a prediction section 77 allowing the trainee to enter, for example, trainee predictions 58 including a trainee predicted "after-recall" assessment indicating a predicted finding after a recall of the patient for additional imaging and diagnosis. This predicted finding after-recall will be in the form of a BI-RADS category, for example, 2, 4, or 5 per Table I above. Category 4 may be broken out into subcategories 4a, 4b, and 4c. Predicted finding after-recall may be entered by marking one checkbox 78 in a table 81 providing for possible BI-RAD values. The checkbox 78 provides data entry points 52.

A similar table 83 with checkboxes 85 providing data entry points 52 may allow the trainee to predict the likelihood that a biopsy is required and checkboxes 87 of table 89 may allow the entry by the trainee of a predicted type of biopsy that would be required. These data entry points 52 provide numeric values that match the categories of the expert predictions 46 discussed above but may differ in values from the expert predictions 46 of corresponding records.

Figure 4:
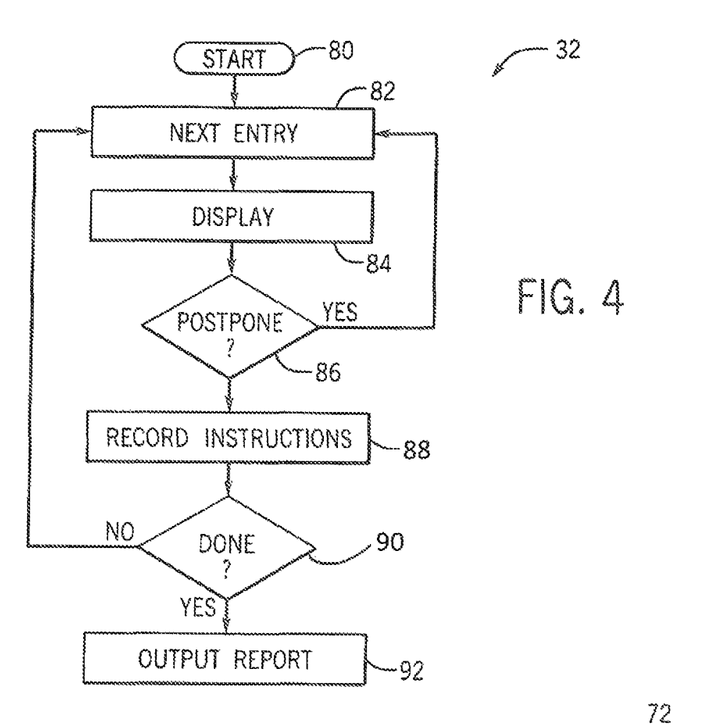
FIG. 4 is a flowchart of the program executed by the computer of FIG. 1 for implementing a simulation session.

Referring now to FIGS. 1 and 4, in a simulation, program 32 may be started by trainee as indicated at process block 80 at a given time allocated for the simulation.

At the start of the simulation and during the simulation, the work monitor 16 provides a list of patient identifiers 41 each representing a case (and underlying records 38) that can be reviewed identified by the trainee. With some exceptions noted below, the trainee will typically move through the list in the order in which they are listed on the work monitor 16.

At process block 82, a current record 38 is identified and the mammographic images 14 for that record 38 are displayed on monitors 12a and 12b per process block 84. Optional clinical data 43 may be also displayed, for example, on either work monitor 16 and 18.

The trainee may postpone analysis of any given case, for example, as indicated by decision block 86, in which case it is put back into a queue represented by the list of patient identifiers 41 and marked as incomplete. This postponed case must be completed before conclusion of the simulation session or counted against the trainee in an ultimate report which will be described. This postponing procedure prevents the trainees from cherry picking what may be perceived as easier cases but allows some flexibility in revisiting conclusions.

For cases that are not postponed, the trainee enters the assessments into the worksheet 50 as indicated by process block 88.

If at decision block 90, the trainee has assessed all of the cases in the simulation data file 34 or a predetermined simulation time has expired, an output report is generated as indicated by process block 92 as will be described below. At early stages of the simulation, however, at decision block 90, the program will then go back to process block 82 and the next record 38 will be presented to the trainee.

Figure 6:
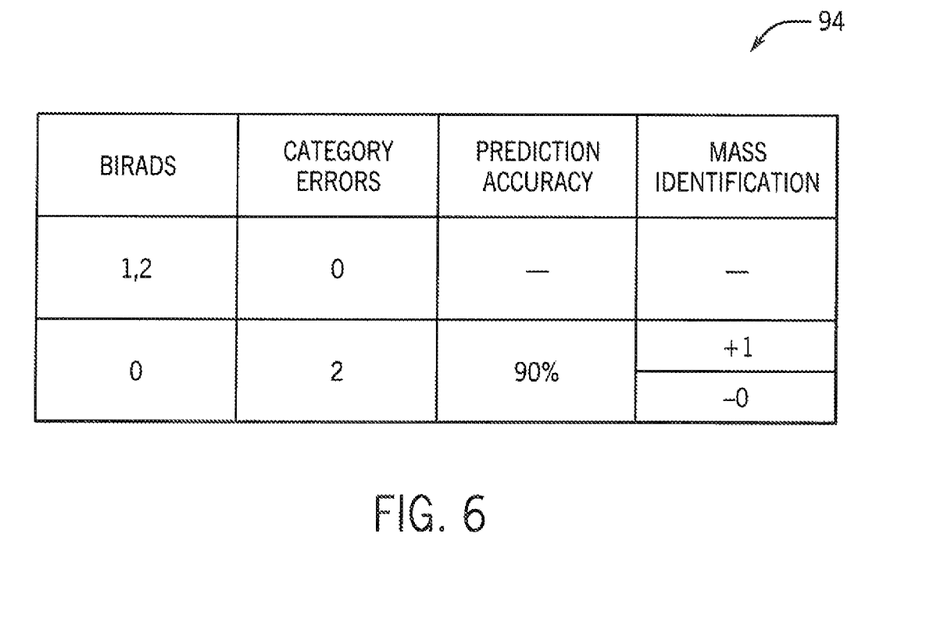
FIG. 6 is an example output report from the screening process. Similar outputs would also be made for diagnostic and other high order breast imaging examinations.

Referring now to FIG. 6, the report 94 generated at process block 92 in its simplest form may provide a table indicating in a first column all possible values of BI-RAD categories for the trainee recall instruction 56. In this case BI-RADS category is 1 and 2 may be grouped together in one row and BI-RADS category 0 separated on a second row. A second column may then indicate the number of times that the trainee recall instructions 56 deviated from the expert recall instructions 44. Cases that were not fully reviewed by the trainee will count as category errors as well as cases with substantive differences in diagnosis. Thus, for example, a trainee recall instruction 56 having a BI-RADS value of zero (recall) will count as an error when compared to an expert recall instruction 44 having a BI-RADS value of 1 or 2. On the other hand, a trainee recall instruction 56 having a BI-RADS value of 1 (normal) will not count as an error when compared to an expert recall instruction 44 having a BI-RADS value of 1 or 2.

Provision may be made to allow the trainee to review those cases where deviations occurred and compare them against the expert values. Notably, however, the total number of records, in any given category is not revealed to prevent possible future case counting by individuals in the simulation.

In addition, a third column may indicate prediction accuracy by the trainee with respect to a comparison of trainee predictions 58 and corresponding expert predictions 46. In one embodiment, this prediction accuracy number may be calculated by assigning every correct prediction a value of 100 and for cases where the trainee predictions 58 and expert predictions 46 deviated, subtracting from this 100 value 25 times the difference between the trainee predictions 58 and the expert predictions 46. These weighted accuracy values may then be totaled and divided by the number of records 38 times 100 to obtain the prediction accuracy. Separate prediction accuracy may be provided for each of the different types of predictions including BI-RADS predictions, biopsy predictions and biopsy type predictions. Again, the provisions may be made to allow the trainee to review those cases where deviations occur and to compare them against the expert values.

Figure 5:
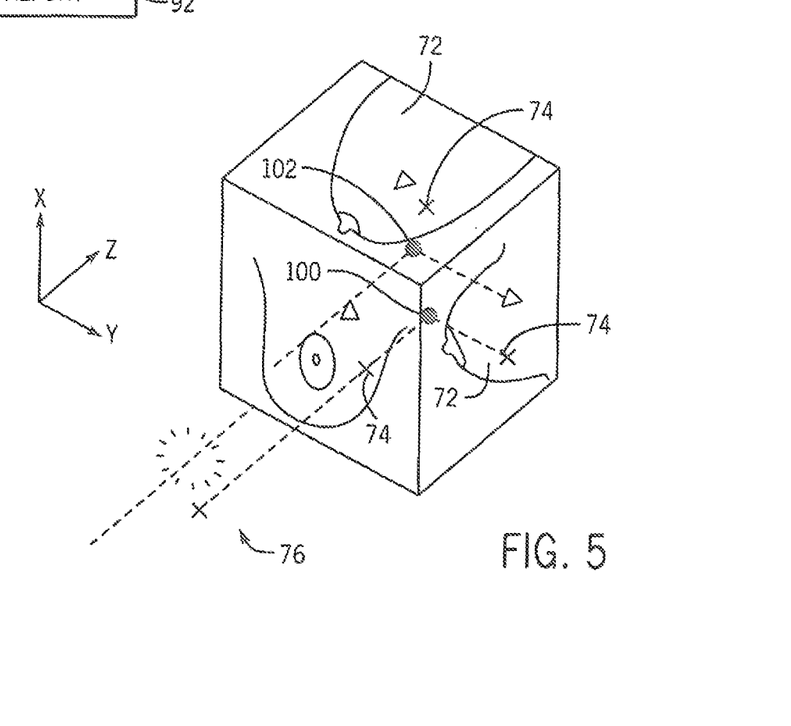
FIG. 5 is a simplified perspective view of a technique for comparing expert- and trainee-identified breast imaging finding locations for quantitative scoring.

Referring now to FIGS. 3, 5, 6, as noted above, the markers 74 entered by the trainee in the worksheet 50 report input monitor 18, and stored at attribute 40g, may be used to establish a three dimensional location 100 within a Cartesian coordinate system defined by the simplified images 72 of the suspicious mass identified by the trainee. Similar information stored at attribute 54e of the trainee data file 36 provides a second location 102 for an expert-located suspicious mass. The vector difference between these two locations 100 and 102 may be compared against a predetermined accuracy threshold to see if a suspicious mass has been properly located.

If a suspicious mass is identified by the trainee and located within the predetermined accuracy threshold with respect to each location 102, no error is indicated. If a suspicious mass is identified outside of the predetermined accuracy threshold or no suspicious mass is identified corresponding to a mass at location 102, a false negative or missed mass is identified in the fourth column of report 94 (with a predicate −). If a suspicious mass is identified having no corresponding location 102, a false positive is indicated at report 94 (with a predicate +).

In the event that multiple masses are present, each location 100 is compared to one closest location 102 for this purpose.

Generally, the output report may satisfy' part of an audit under the Mammographic Quality Standards Act (MQSA). In this regard, the trainee may obtain all or part of the output report and may provide information such as recall rate, PPV, cancer detection rate and more.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

I claim:

1. A simulator for breast imaging examination comprising:
   a medical grade computer display;
   a data input device; and
   an electronic computer communicating with the medical grade computer display and the data input device, the electronic computer including:
   (a) an electronic memory system holding a data structure having multiple records linking mammographic images related to actual patients having pre-recall information including a medical history and post-recall information including a final diagnostic conclusion of breast cancer, to expert recall instructions prepared by a healthcare provider reviewing the mammographic images without knowledge of the post-recall information, the expert recall instructions providing a healthcare provider's professional judgment of whether a patient associated with a given mammographic image should be recalled for additional imaging based on the mammographic image but not the post-recall information wherein at least some expert recall instructions are different than recall instructions that would be made based on the final diagnostic conclusion, the electronic memory system further holding a stored program;
   (b) an electronic processor executing the stored program to successively read the records of the data structure to:
   (i) display the given mammographic image;
   (ii) receive input through the data input device indicating a trainee recommended recall instruction providing a trainee's judgment of whether the patient associated with the given mammographic image should be recalled for additional imaging based on the mammographic image;
   (iii) compare the trainee recommended recall instruction and the expert recall instruction;
   (iv) repeat steps (i)-(iii) for multiple mammographic images; and (v) output a report indicating divergence between the trainee recommended recall instructions and the expert recall instructions represented by a number of discrepancies between the expert recall instructions and the trainee recall instructions.

2. The simulator for breast imaging examination of claim 1 wherein records of the data structure provide expert recall instructions that are predominantly instructions for no recall.

3. The simulator for breast imaging examination of claim 2 wherein the records of the data structure provide expert recall instructions instructing recall of the patient greater than a normal expected percentage of five to twelve percent.

4. The simulator for breast imaging examination of claim 3 wherein greater than 20 percent of the records of the data structure provide for expert recall instructions instructing recall of the patient.

5. The simulator for breast imaging examination of claim 3 wherein the recall instructions are encoded as numeric BI-RAD scores.

6. A simulator for breast imaging examination comprising:
  a medical grade computer display;
  a data input device; and
  an electronic computer communicating with the medical grade computer display and the data input device, the electronic computer including:
    (a) an electronic memory system holding a data structure having multiple records linking mammographic images, related to actual patients having pre-recall information including a medical history and post-recall information including a final diagnostic conclusion of breast cancer, to expert recall instructions and expert after-recall instructions prepared by a healthcare provider reviewing the mammographic images without knowledge of the post-recall information, the expert recall instructions providing a healthcare provider's professional judgment of whether a patient associated with a given mammographic image should be recalled for additional imaging based on the mammographic image but not the post-recall information wherein at least some expert recall instructions are different than recall instructions that would be made based on the final diagnostic conclusion and the expert after-recall instructions providing a healthcare provider's professional judgment of the ultimate breast cancer assessment of the patient wherein at least some expert after-recall instructions are different from the final diagnostic conclusion of breast cancer, the electronic memory system further holding a stored program;
    (b) an electronic processor executing the stored program to successively read the records of the data structure to:
      (i) display the given mammographic image;
      (ii) receive input through the data input device indicating a trainee recommended recall instruction providing a trainee's judgment of whether the patient associated with the given mammographic image should be recalled for additional imaging based on the mammographic image;
      (iii) receive input through the data input device indicating a trainee predicted after-recall assessment providing a trainee's judgment of an ultimate breast cancer assessment after the patient of the record is recalled for further imaging;
      (iv) compare the trainee recommended recall instructions and the expert recall instructions;
      (v) compare the trainee predicted after-recall instructions and the expert after-recall instructions;
      (vi) repeat steps (i)-(v) for multiple mammographic images; and
      (vii) output a report indicating divergence between the trainee recommended recall instructions and the expert recall instructions represented by a number of discrepancies between the expert recall instructions and the trainee recall instructions and a divergence between trainee predicted after-recall assessment and expert after-recall assessment represented by a number of discrepancies between the expert after-recall instructions and the trainee after-recall instructions.

7. The simulator for breast imaging examination of claim 6 wherein the predicted after-recall assessment are encoded as numeric BI-RAD scores.

8. The simulator for breast imaging examination of claim 6 wherein the predicted after-recall assessment includes at least one of a numeric likelihood of biopsy and a numerically encoded type of biopsy.

9. The simulator for breast imaging examination of claim 1 wherein step (ii) further receives input through the data input device indicating a trainee-determined location of suspicious imaging finding in the breast imaging examination of each record and wherein the records of the data structure further provide expert-determined location of suspicious imaging finding in the breast imaging examination of each record;
  and wherein the output report indicates a divergence between trainee-determined location of suspicious imaging findings and expert-determined location of suspicious imaging findings informed by positional error between the trainee-determined location of suspicious imaging findings and the expert location of suspicious imaging findings.

10. The simulator for breast imaging examination of claim 1 further including a standard monitor communicating with the computer and wherein the standard monitor further displays a patient clinical history associated with each record.

11. The simulator for breast imaging examination of claim 1 wherein the records of the data structure provide records reflecting a normal age distribution.

12. The simulator for breast imaging examination of claim 1 wherein the records of the data structure provide records reflecting a normal breast-type distribution.

13. The simulator for breast imaging examination of claim 1 wherein the data structure includes no less than 50 records.

14. The simulator for breast imaging examination of claim 1 wherein the electronic computer further executes the stored program to provide a time limit for performing steps (i)-(iii) for the records.

15. The simulator for breast imaging examination of claim 14 wherein the electronic processor executes the program to allow step (ii)-(iii) to be postponed for a given record displayed according to step (i) until after completion of steps (i)-(iii) for later displayed records but includes the given record in the report of step (vii) regardless of whether it is subsequently completed.

16. The simulator for breast imaging examination of claim 1 wherein the medical grade computer display provides a minimum resolution of five megapixels.

17. The simulator for breast imaging examination of claim 1 wherein the mammographic images indicate imaging parameters selected from the group consisting of: laterality, image view, and radiation dose parameters (kVp, milliamps, compression thickness target and filter).

18. A method of simulating breast imaging examination using a simulator having:
 a medical grade computer display;
 a data input device; and
 an electronic computer communicating with the medical grade computer display and the data input device, the electronic computer including:
  an electronic memory system holding a data structure having multiple records linking breast imaging examinations, related to actual patients having pre-recall information including a medical history and post-recall information including a final diagnostic conclusion of breast cancer, to expert recall instructions prepared by a healthcare provider reviewing the mammographic images without knowledge of the post-recall information, the expert recall instructions providing a healthcare provider's professional judgment of whether a patient associated with a given breast imaging examination should be recalled for additional imaging based on the presented breast imaging examination but not the post-recall information wherein at least some expert recall instructions are different than recall instructions that would be made based on the final diagnostic conclusion, the electronic memory system further holding a stored program;
  an electronic processor executing the stored program to successively read the records of the data structure to:
   display the given mammographic image;
   receive input through the data input device indicating a trainee recommended recall instruction providing a trainee's judgment of whether the patient associated with the given mammographic image should be recalled for additional imaging based on the mammographic image;
   compare the trainee recommended recall instruction and the expert recall instruction;
   output a report indicating divergence between the trainee recommended recall instruction and the expert recall instruction;
 the method comprising the steps of:
 executing the stored program with the electronic processor to:
  (a) display at least one breast imaging examination of the record;
  (b) receive input through the trainee input device indicating a trainee recommended recall instruction;
  (c) compare the trainee recommended recall instructions and the expert recall instructions; and
  (d) output a report indicating divergence between the trainee recommended recall instructions and the expert recall instructions represented by a number of discrepancies between the expert recall instructions and the trainee recall instructions.

19. The simulator for breast imaging examination of claim 1 wherein the data structure stores patients' medical histories and the electronic processor displays the patient's medical history.

20. The simulator for breast imaging examination of claim 19 wherein the trainee recommended recall instruction is also based on the medical history of the patient.

* * * * *